(12) United States Patent
Sato et al.

(10) Patent No.: US 9,138,203 B2
(45) Date of Patent: Sep. 22, 2015

(54) ULTRASONIC PROBE AND ULTRASONIC IMAGING APPARATUS USING THE SAME

(75) Inventors: Masahiro Sato, Tokyo (JP); Akifumi Sako, Tokyo (JP); Kazunari Ishida, Tokyo (JP); Hiroki Tanaka, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 437 days.

(21) Appl. No.: 13/581,441

(22) PCT Filed: Feb. 17, 2011

(86) PCT No.: PCT/JP2011/053321
§ 371 (c)(1),
(2), (4) Date: Aug. 27, 2012

(87) PCT Pub. No.: WO2011/105269
PCT Pub. Date: Sep. 1, 2011

(65) Prior Publication Data
US 2012/0320710 A1 Dec. 20, 2012

(30) Foreign Application Priority Data
Feb. 26, 2010 (JP) ................. 2010-041838

(51) Int. Cl.
 G03B 42/06 (2006.01)
 G01N 29/09 (2006.01)
 A61B 8/00 (2006.01)
 G10K 11/00 (2006.01)
 G01S 15/89 (2006.01)
(52) U.S. Cl.
 CPC ........... *A61B 8/4483* (2013.01); *G01S 15/8915* (2013.01); *G10K 11/002* (2013.01)

(58) Field of Classification Search
 CPC . G01S 15/8915; A61B 8/4483; G10K 11/002
 USPC ..................................... 367/7, 140
 See application file for complete search history.

(56) References Cited

U.S. PATENT DOCUMENTS 6,714,484 B2    3/2004   Laudabaum et al.
6,831,394 B2   12/2004   Baumgartner
8,975,713 B2 *  3/2015   Sako et al. .............. 600/437
(Continued)

FOREIGN PATENT DOCUMENTS

CN    101172044 A    5/2008
CN    201261009 Y    6/2009
(Continued)

OTHER PUBLICATIONS

International Search Report from International Application No. PCT/JP2011/053321 mailed Apr. 26, 2011.
(Continued)

*Primary Examiner* — Daniel Pihulic
(74) *Attorney, Agent, or Firm* — Brundidge & Stanger, P.C.

(57) ABSTRACT

In order to provide an ultrasonic probe capable of suppressing the influence of multiple reflections occurring on the interface of a transducer with a CMUT chip and a backing layer, an ultrasonic probe of the present invention has a structure where an acoustic lens 14, transducers 11-1 to 11-*m*, and a backing layer 12 are laminated. Each of the transducers 11-1 to 11-*m* has a CMUT chip, and the backing layer 12 is formed of a material with a value of substantially the same acoustic impedance as the acoustic lens 14.

14 Claims, 15 Drawing Sheets

(56) References Cited

U.S. PATENT DOCUMENTS

| | | | |
|---|---|---|---|
| 2004/0174773 A1 | 9/2004 | Thomenius et al. | |
| 2004/0215079 A1* | 10/2004 | Omura et al. | 600/459 |
| 2006/0232164 A1 | 10/2006 | Kondo et al. | |
| 2007/0016064 A1* | 1/2007 | Yamashita et al. | 600/459 |
| 2009/0069486 A1* | 3/2009 | Yamashita et al. | 524/440 |
| 2010/0198070 A1* | 8/2010 | Asafusa et al. | 600/459 |
| 2011/0071396 A1* | 3/2011 | Sano et al. | 600/443 |
| 2012/0320710 A1* | 12/2012 | Sato et al. | 367/7 |

FOREIGN PATENT DOCUMENTS

| | | | |
|---|---|---|---|
| CN | 102770078 A | * | 11/2012 |
| EP | 1591067 A1 | | 11/2005 |
| EP | 2540227 A1 | * | 1/2013 |
| JP | 2005125071 A | | 5/2005 |
| JP | 2005-295553 | | 10/2005 |
| JP | 2007125225 | | 5/2007 |
| JP | 2008-119318 | | 5/2008 |
| JP | 2008119318 | | 5/2008 |
| JP | 2009-112379 | | 5/2009 |
| JP | 2009112379 | | 5/2009 |
| JP | 2010042093 | | 2/2010 |
| WO | 2005032371 A1 | | 4/2005 |
| WO | 2009/069281 | | 11/2008 |
| WO | WO 2011105269 A1 | * | 9/2011 |

OTHER PUBLICATIONS

Foreign Office Action with attached English translation, 4 pages, dated Jan. 27, 2015.

* cited by examiner

US 9,138,203 B2

ULTRASONIC PROBE AND ULTRASONIC IMAGING APPARATUS USING THE SAME

TECHNICAL FIELD

The present invention relates to an ultrasonic probe which uses a capacitive transducer CMUT chip (Capacitive Micromachined Ultrasound Transducer) chip in a transducer and in particular, to a technique for suppressing multiple reflections.

BACKGROUND ART

A piezoelectric element has been used as a material of a transducer in an ultrasonic probe in the related art. In recent years, a CMUT chip formed by a semiconductor device has been adopted as a transducer of an ultrasonic probe.

In the case of the CMUT chip, acoustic-electric conversion efficiency of the transducer is low compared with a piezoelectric element. For this reason, the CMUT chip has a technical problem in that it is easier to cause multiple reflections than the piezoelectric element.

The multiple reflections are a phenomenon in which reflection of ultrasonic waves on a reflective surface is repeated with the boundary of tissue or the like in an object as the reflective surface. This means a phenomenon in which artifacts of a structure, which is not present in the measurement range of an ultrasonic probe, appear.

Therefore, in order to solve the problem of multiple reflections of a transducer having a CMUT chip, PTL 1 discloses a technique of reducing the multiple reflections of a transducer per channel by meeting both the following first and second conditions.

Firstly, the first condition is to satisfy the condition of $6.5/fc < \alpha d$ where the absorption coefficient of the acoustic lens is $\alpha$ [dB/mm/MHz], the maximum thickness of the acoustic lens is d [mm], and the center frequency of the transducer is fc [MHz].

Then, the second condition is to satisfy the condition $L < 1/((3\pi fc)^2 \times C)$ where the inductance value of the transducer per channel is L [H], the capacitance of the transducer per channel is C [pF], and the center frequency of the transducer is fc [MHz].

CITATION LIST

Patent Literature

[PTL 1] WO2009/069281
[PTL 2] U.S. Pat. No. 6,831,394
[PTL 3] U.S. Pat. No. 6,714,484

SUMMARY OF INVENTION

Technical Problem

PTL 1 is countermeasure technology of multiple reflections that occur when reflected waves caused by acoustic impedance mismatch between an acoustic lens and a transducer on the interface of the acoustic lens and the transducer are retransmitted to an object.

Accordingly, PTL 1 does not disclose multiple reflections that occur when reflected waves caused by acoustic impedance mismatch between a transducer and a backing layer on the interface of the transducer and the backing layer reach the object.

Therefore, it is an object of the present invention to provide an ultrasonic probe capable of suppressing the influence of multiple reflections, which occur on the interface of a transducer with a CMUT chip and a backing layer, and an ultrasonic diagnostic apparatus using the same.

Solution to Problem

In order to achieve the above-described object, an ultrasonic probe of the present invention has a structure where an acoustic lens, a transducer, and a backing layer are laminated and is characterized in that the transducer has a CMUT chip and the backing layer is formed of a material with a value of substantially the same acoustic impedance as the acoustic lens.

First, a direction from the transducer to the acoustic lens layer side (side on which the object is present) is defined as a first direction, and a direction from the transducer to the backing layer side (opposite side to the side on which the object is present) is defined as a second direction.

The reason why the backing layer is formed of a material with substantially the same acoustic impedance as the acoustic lens is that, since the amount of change in acoustic impedance is the same in the first and second directions, acoustic energy of reflected waves is distributed at the same rate in the first and second directions.

Accordingly, on the interface of the transducer and the backing layer, only the acoustic energy of some distributed reflected waves propagates in the second direction. As a result, it is possible to suppress the occurrence of multiple reflections caused on the interface of the transducer and the backing layer.

Advantageous Effects of Invention

According to the present invention, the effect of providing the ultrasonic probe capable of suppressing the influence of multiple reflections, which occur on the interface of the transducer with the CMUT chip and the backing layer, and the ultrasonic diagnostic apparatus using the same is obtained.

DESCRIPTION OF EMBODIMENTS

An ultrasonic diagnostic apparatus which adopts an ultrasonic probe of the present invention will be described in detail using the drawings.

First, the schematic configuration of the ultrasonic diagnostic apparatus will be described using FIG. 1.

Figure 1:
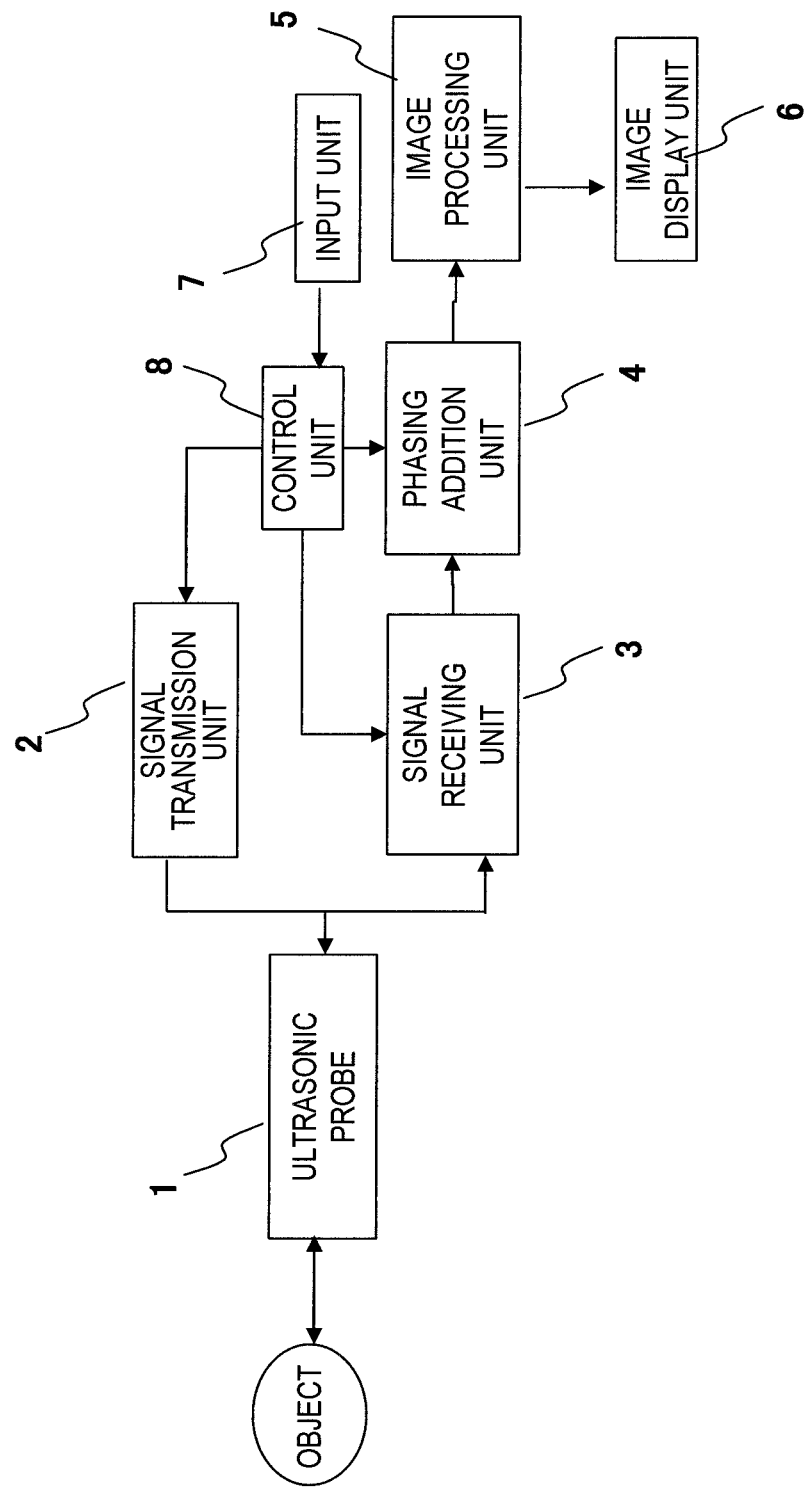
FIG. 1 is a view showing the schematic configuration of an ultrasonic diagnostic apparatus in which the invention has been adopted.

FIG. 1 is a view showing the schematic configuration of the ultrasonic diagnostic apparatus which adopts the present invention.

The ultrasonic diagnostic apparatus includes an ultrasonic probe 1, a signal transmission unit 2, a signal receiving unit 3, a phasing addition unit 4, an image processing unit 5, an image display unit 6, an input unit 7, and a control unit 8.

In a state where the ultrasonic probe 1 is brought into contact by the examiner with the surface of an object where a portion to be imaged is present, the ultrasonic probe 1 transmits an ultrasonic wave to a photographing portion, receives a reflected wave transmitted from the photographing portion, and converts the reflected wave into an electric signal called a reflection echo signal.

The signal transmission unit 2 transmits an ultrasonic wave to the ultrasonic probe 1, which is electrically connected to the signal transmission unit 2, toward the object so as to be focused on the depth at which a photographing portion is present, at the timing of ultrasonic wave transmission.

The signal receiving unit 3 receives a reflection echo signal from the ultrasonic probe 1 at the timing of ultrasonic wave reception and performs signal processing including signal amplification and analog to digital conversion.

The phasing addition unit 4 performs phasing addition of the reflection echo signal signal-processed by the signal receiving unit 3.

The image processing unit 5 converts the reflection echo signal after phasing addition in the phasing addition unit 4 into an ultrasonic image.

The image display unit 6 displays the ultrasonic image converted by the image processing unit 5.

The input unit 7 inputs information of a portion to be imaged or an ultrasonic probe in use, which is required when the examiner converts the ultrasonic image.

The control unit 8 performs the following control on the basis of the information input through the input unit 7.

(1) Control to repeat the timing of transmission and reception of an ultrasonic wave at predetermined intervals.

(2) Control to make the signal transmission unit 2 transmit an ultrasonic wave toward the object at the signal transmission timing.

(3) Control to make the signal receiving unit 3 perform signal processing on the reflection echo signal at the signal receiving timing.

(4) Control to make the phasing addition unit 4 perform phasing addition of the reflection echo signal.

(5) Control to make the image processing unit 5 convert the reflection echo signal after phasing addition into an ultrasonic image.

(6) Control to make the image display unit 6 display the ultrasonic image.

Next, an example of the configuration of the ultrasonic probe 1 will be described using FIGS. 2 to 4.

Figure 2:
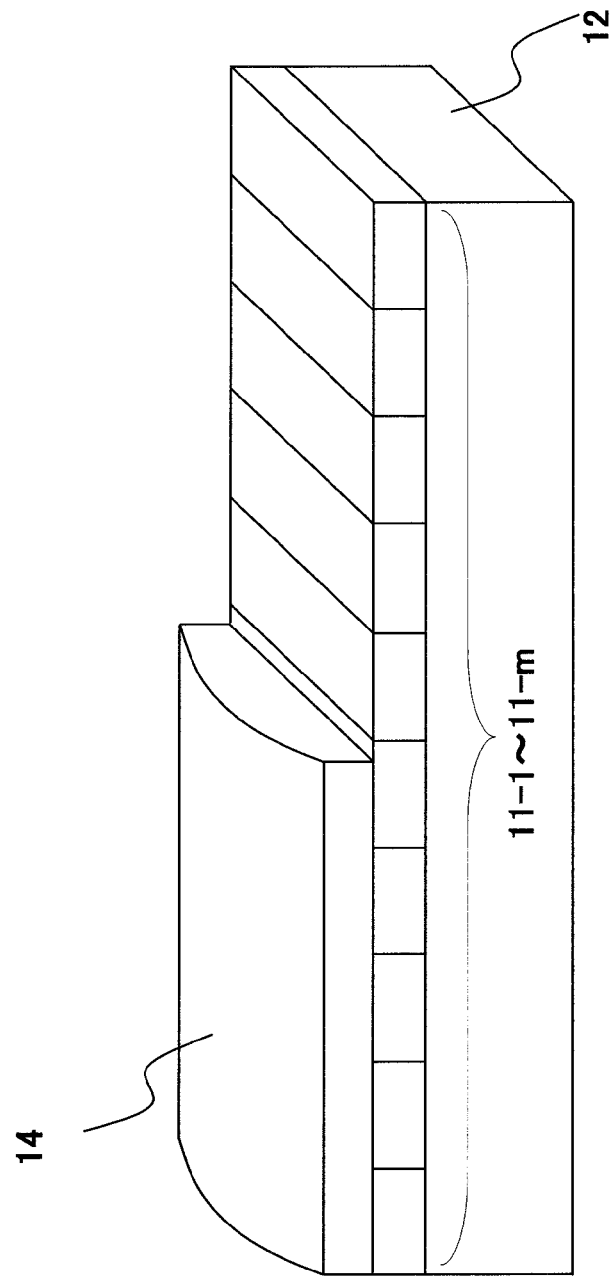
FIG. 2 is a view showing an example of the structure of a linear ultrasonic probe which uses a plurality of CMUT chips in a transducer of an ultrasonic probe.

FIG. 2 is a view showing an example of the structure of a linear ultrasonic probe which uses a plurality of CMUT chips in a transducer of the ultrasonic probe. FIG. 3 is a top view of transducers 11-1 to 11-$m$, and FIG. 4 is a cross-sectional view of a CMUT chip 18 which forms the transducer 11-1 or the like shown in FIG. 2.

The ultrasonic probe 1 has a one-dimensional array structure where "m" strip-shaped transducers 11-1 to 11-$m$ (m is a natural number, for example, 64 or 192) are arrayed, and a backing layer 12 is disposed on the back of each of the transducers 11-1 to 11-$m$. In addition, an acoustic lens 14 is disposed at the transmission side of an ultrasonic wave of the transducers 11-1 to 11-$m$ (upper side in FIG. 2). The transducers 11-1 to 11-$m$ convert an electric carrier signal into an ultrasonic wave and transmit the ultrasonic wave into the body and also receive an ultrasonic wave reflected in the body and convert the reflected ultrasonic wave into an electric signal to form a reflected signal.

The backing layer 12 is disposed in order to absorb unnecessary ultrasonic waves transmitted to the back side of each of the transducers 11-1 to 11-$m$ and to suppress unnecessary vibration of the transducers 11-1 to 11-$m$.

The acoustic lens 14 converges ultrasonic beams in a so-called short axis direction perpendicular to the arrangement direction of the transducers 11-1 to 11-$m$.

Figure 3:
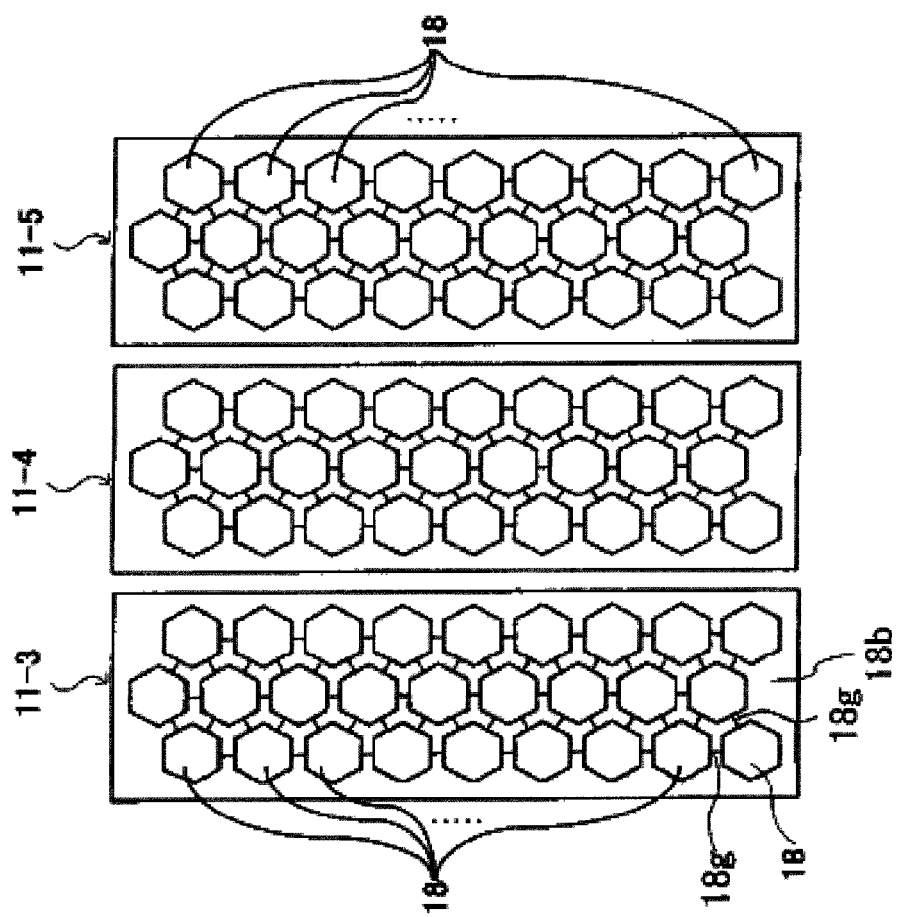
FIG. 3 is a top view of transducers 11-1 to 11-m.
Figure 4:
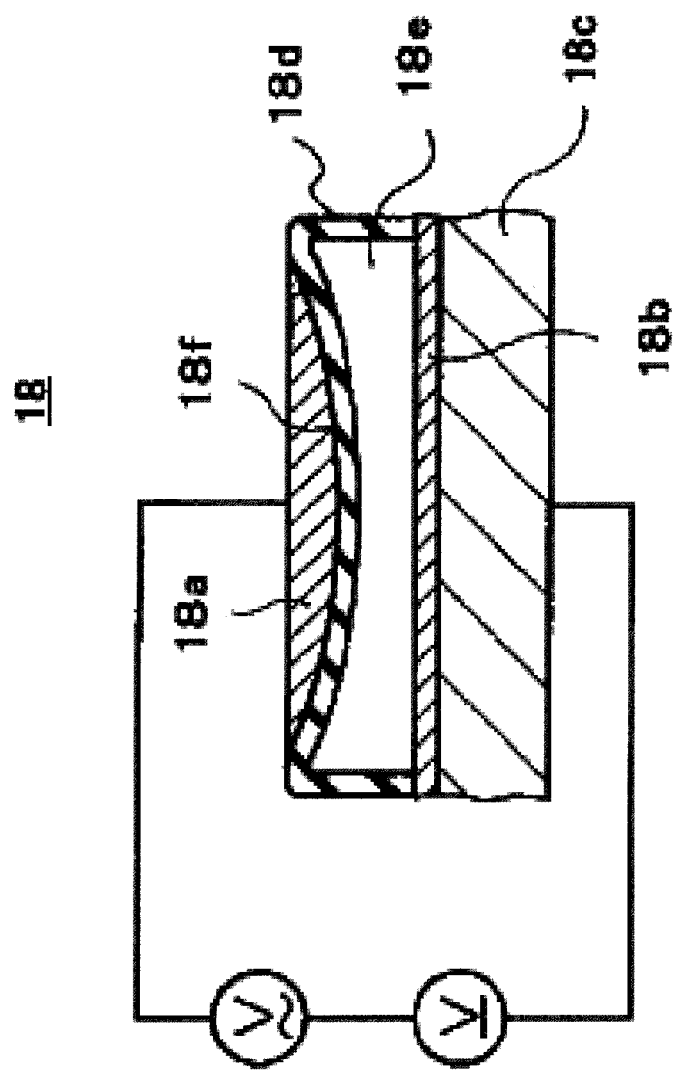
FIG. 4 is a cross-sectional view of a CMUT chip 18 which forms the transducer 11-1 or the like shown in FIG. 2.

Here, as shown in FIG. 3, each of the transducers 11-1 to 11-$m$ is formed by a plurality of hexagonal micro CMUT chips 18, for example (in addition, in FIG. 3, only three elements of the transducers 11-3 to 11-5 are shown for the sake of illustration). As will be described later using FIG. 4, each CMUT chip 18 is electrically considered as a capacitor. Meanwhile, in a group of CMUT chips 18 included in each of the transducers 11-1 to 11-$m$, upper electrodes 18$a$ are connected to each other by wiring lines 18$g$ and a lower electrode 18$b$ is a common electrode. Accordingly, each CMUT chip 18 has the same electrical function as a plurality of parallel capacitors.

The structure of one CMUT chip 18 will be described using FIG. 4. The CMUT chip 18 is formed by semiconductor process microfabrication technology, and includes a substrate 18$c$ which is a semiconductor substrate such as a silicon substrate; the lower electrode 18$b$ formed on the substrate 18$c$; an insulator film 18$d$ serving as a supporting section; a semiconductor thin film 18$f$ disposed on the insulator film 18$d$; and the upper electrode 18$a$ disposed on the semiconductor thin film 18$f$. Between the semiconductor thin film 18$f$ and the lower electrode 18$b$, a hole 18$e$ in a vacuum state (or with predetermined gas pressure) formed by etching the insulator film 18$d$ is provided.

The edge of the semiconductor thin film 18$f$, which is formed of compound semiconductor or the like, is supported by the insulator film 18$d$. Accordingly, the semiconductor thin film 18f has a stretched shape floating in space just like a drum of musical instruments. When a DC bias voltage is applied between the upper electrode 18a and the lower electrode 18b, Coulomb force is generated. Accordingly, moderate tension occurs in the semiconductor thin film 18f. At the time of transmission of an ultrasonic wave, when a driving AC signal is applied between the upper electrode 18a and the lower electrode 18b so as to be superimposed on the DC-bias voltage, an ultrasonic wave is generated from the CMUT chip 18 in the same manner as when a drum of musical instruments is repeatedly hit to emit a sound. In addition, at the time of reception of an ultrasonic wave, when an ultrasonic wave is incident on the CMUT chip 18, the distance between the electrode 18a and 18b changes in proportion to the size and the waveform. Accordingly, the capacitance of a capacitor formed by both the electrodes 18a and 18b changes according to the distance change. The ultrasonic wave can be receivable by detecting the capacitance change from the electric signals of both the electrodes 18a and 18b. As shown in FIG. 3, each of the transducers 11-1 to 11-m has a configuration in which the plurality of CMUT chips 18 is arrayed in parallel. Therefore, it is possible to generate ultrasonic signals simultaneously from the plurality of CMUT chips 18 and transmit the ultrasonic signals into the body, or it is possible to receive signals simultaneously in the plurality of CMUT chips 18 and form reflected signals.

Figure 5:
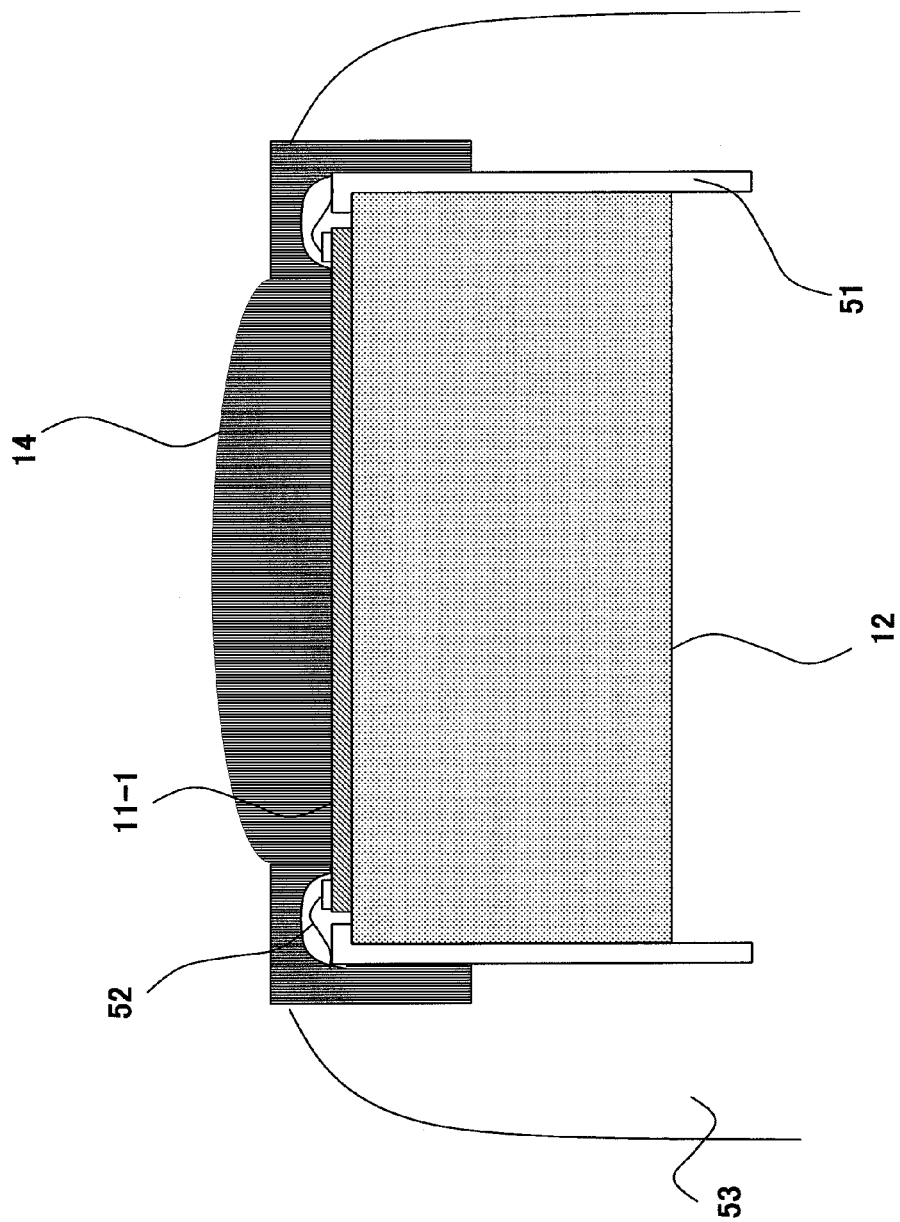
FIG. 5 is a cross-sectional view of an ultrasonic probe of one channel.

FIG. 5 is a cross-sectional view of a portion of the transducer 11-1 among the "m" transducers 11-1 to 11-m, that is, an ultrasonic probe of one channel.

The acoustic lens 14 (upper side in the drawing) is formed on the transducer 11-1, and the backing layer 12 (lower side in the drawing) is formed below the transducer 11-1. A flexible base 51 is provided in a range from the top periphery of the backing layer 12 to the side surface, and applies a bias voltage and a driving voltage for driving the CMUT chip 18. A metal wire 52 is connected to the flexible base 51 by the upper and lower electrodes of the transducer 11-1. A probe cover 53 is provided at the side surface of the probe, and serves as a grasping portion of the ultrasonic probe for the examiner.

Figure 6:
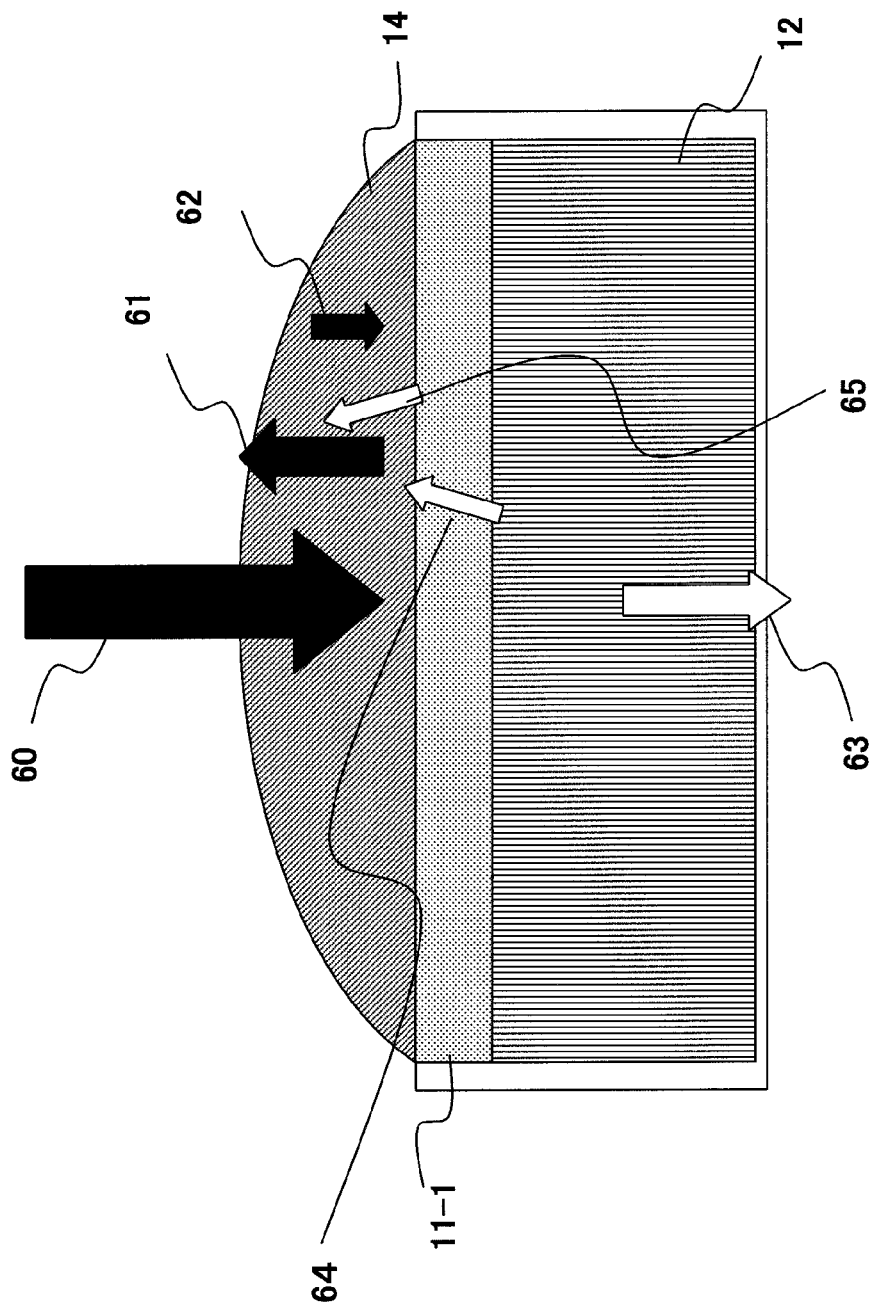
FIG. 6 is a view for explaining the principle of multiple reflections using the model in FIG. 5.

FIG. 6 is a view for explaining the principle of multiple reflections using the model in FIG. 5.

The ultrasonic probe captures an ultrasonic image by making the acoustic lens 14 in contact with an object. In FIG. 6, an object is not shown for the sake of simplicity.

First, the control unit 8 of the ultrasonic diagnostic apparatus makes the ultrasonic probe 1 transmit ultrasonic waves to the object. The ultrasonic probe 1 receives reflection echo signals 60 from the object.

Then, some reflection echo signals 60 are converted into electric signals by acoustic-electric conversion of the transducer 11-1, and the electric signals are converted into an ultrasonic image through signal processing. However, some of the reflection echoes 60 are retransmitted to the object as retransmitted waves 61. The retransmitted waves 61 are reflected again from the object and arrive at the surface of the acoustic lens 14 as multiple reflection echoes 62.

Then, for the multiple reflection echo 62, a phenomenon in the boundary between the transducer 11-1 and the backing layer 12 with different acoustic impedance will be described.

Some reflection echo signals 60 are waves 63 transmitted through the backing layer 12, and are absorbed by the backing layer 12. In addition, some multiple reflection echoes 62 are reflected as reflected waves 64 due to acoustic impedance mismatch between the transducer 11-1 and the backing layer 12. The reflected wave 64 is combined with a reflected wave 65, which is generated due to acoustic impedance mismatch between the acoustic lens 14 and the transducer 11-1, to generate a retransmitted wave 61.

In addition, since the CMUT chip 18 of the transducer 11-1 has a hole 18e, the hole 18e of the CMUT chip 18 acts as a transmission path of acoustic energy from the backing layer 12 to the acoustic lens 14.

Accordingly, since it can be said that the influence of the reflected wave 64 from the boundary between the transducer 11-1 having the CMUT chip 18 and the backing layer 12 is large compared with that in the case of a transducer having a piezoelectric element, more measures against the reflected waves from the boundary between the transducer 11-1 and the backing layer 12 are needed in the transducer 11-1 using the CMUT chip 18.

Next, the principle of FIG. 6 will be described using Expressions.

The amplitude ratio of the multiple reflection echo 62 to the reflection echo 60 is equal to or less than the product of the reflectance R and the square of the sound attenuation rate α of the acoustic lens, and this is expressed by Expression (1). The reflectance R is obtained by removing signal components of the reflected waves 64 from the sum of components of the signals 63 absorbed by the backing layer 12 and signal components of the reflected waves 64 in the boundary between the transducer 11-1 and the backing layer 12.

[Expression 1]

$$\frac{\text{amplitude of multiple reflection echo}}{\text{amplitude of reflection echo}} \leq R\alpha^2 \quad (1)$$

Moreover, according to empirical assumptions regarding the ultrasonic diagnostic apparatus, generally, if the amplitude ratio of the reflection echo 60 and the multiple reflection echo 62 becomes equal to or less than a decibel value of −20 dB, the influence on an ultrasonic image does not appear. Accordingly, Expression (2) is obtained by transforming Expression (1) to a logarithm in consideration of the reduction of the multiple reflection echo 62.

[Expression 2]

$$20\, \mathrm{Log}_{10}(R\alpha^2) \leq -20 \quad (2)$$

In addition, if the logarithm of Expression (2) is expanded, Expression (3) is obtained.

[Expression 3]

$$20\, \mathrm{Log}_{10} R + 2 \cdot 20\, \mathrm{Log}_{10} \alpha \leq -20 \quad (3)$$

Here, assuming that the attenuation rate of the acoustic lens 14 converted into the decibel value is β [dB·MHz/mm], the thickness of the acoustic lens 14 is d [mm], and the center frequency of a probe is fc [MHz], Expression (4) is obtained by transforming Expression (3) using the fact that the decibel conversion value $20\, \mathrm{Log}_{10}\alpha$ of the sound attenuation rate α is expressed as −βdfc.

[Expression 4]

$$20\, \mathrm{Log}_{10} R - 2\beta dfc \leq -20 \quad (4)$$

In addition, if Expression (4) is converted into an exponential function, Expression (5) is obtained.

[Expression 5]

$$R \leq 10^{\left(\frac{\beta d f_C - 10}{10}\right)} \quad (5)$$

Accordingly, if the apparent reflectance R from the acoustic lens 14 of the ultrasonic probe is set so as to satisfy Expression (5), it is possible to reduce the influence of multiple reflection artifacts.

In addition, assuming that the maximum value of the reflectance R is Rmax, Rmax can be expressed by the following Expression (6).

[Expression 6]

$$R\max = 10^{\left(\frac{\beta d f_C - 10}{10}\right)} \quad (6)$$

In addition, the center frequency fc of the ultrasonic probe is set in the range of 2 MHz to 11 MHz. In addition, the thickness d of an acoustic lens is usually approximately 0.5 mm to 1.2 mm. In addition, in an ultrasonic probe used for high-frequency applications, it is necessary to suppress the influence of acoustic lens attenuation. In this case, therefore, the thickness of the acoustic lens is set to 0.5 mm to 0.8 mm which is thinner than in the normal case. Silicon rubber and the like are mainly used as materials of the acoustic lens, and the sound attenuation rate β is 1 dB·MHz/mm.

In the above numeric value range, the maximum value Rmax of the reflectance which satisfies Expression (6) in the above is calculated. Satisfying Expression (6) means suppressing the reflectance with the maximum value Rmax or less in order that there is no influence of multiple reflection artifacts.

For example, the maximum value Rmax of the reflectance is calculated from the center frequency [MHz] and the thickness of the acoustic lens as shown in Table 1.

TABLE 1

| Center frequency [MHz] | Thickness of acoustic lens [mm] | Maximum value Rmax of reflectance |
|---|---|---|
| 11.0 (for high-frequency application) | 0.8 | 0.76 |
| 7.5 (for middle-frequency application) | 1.2 | 0.79 |
| 2.0 (for low-frequency application) | 1.2 | 0.17 |

In addition, the reflectance mr of an ultrasonic wave incident from the acoustic lens side is expressed by the following Expression (7) assuming that the acoustic impedance of the transducer 11-1, the acoustic lens 14, and the backing layer 12 is $Z_1$, $Z_2$, and $Z_3$, respectively, the propagation constant of the transducer 11 is $\gamma_1$, and the thickness of the transducer 11 is $d_1$ (Course of Institute of Electrical Engineers of Japan, electric circuit theory (refer to pp. 298 to 303, second revised edition)).

[Expression 7]

$$mr = \frac{\left(\frac{Z_1 - Z_2}{Z_1 + Z_2}\right) + \left(\frac{Z_3 - Z_1}{Z_3 + Z_1}\right)e^{-2\gamma_1 d_1}}{1 + \left(\frac{Z_1 - Z_2}{Z_1 + Z_2}\right) + \left(\frac{Z_3 - Z_1}{Z_3 + Z_1}\right)e^{-2\gamma_1 d_1}} \quad (7)$$

Next, characteristics of frequency and ultrasonic wave reflectance in a typical model of the transducer 11-1 and the backing layer 12 will be described.

Figure 7:
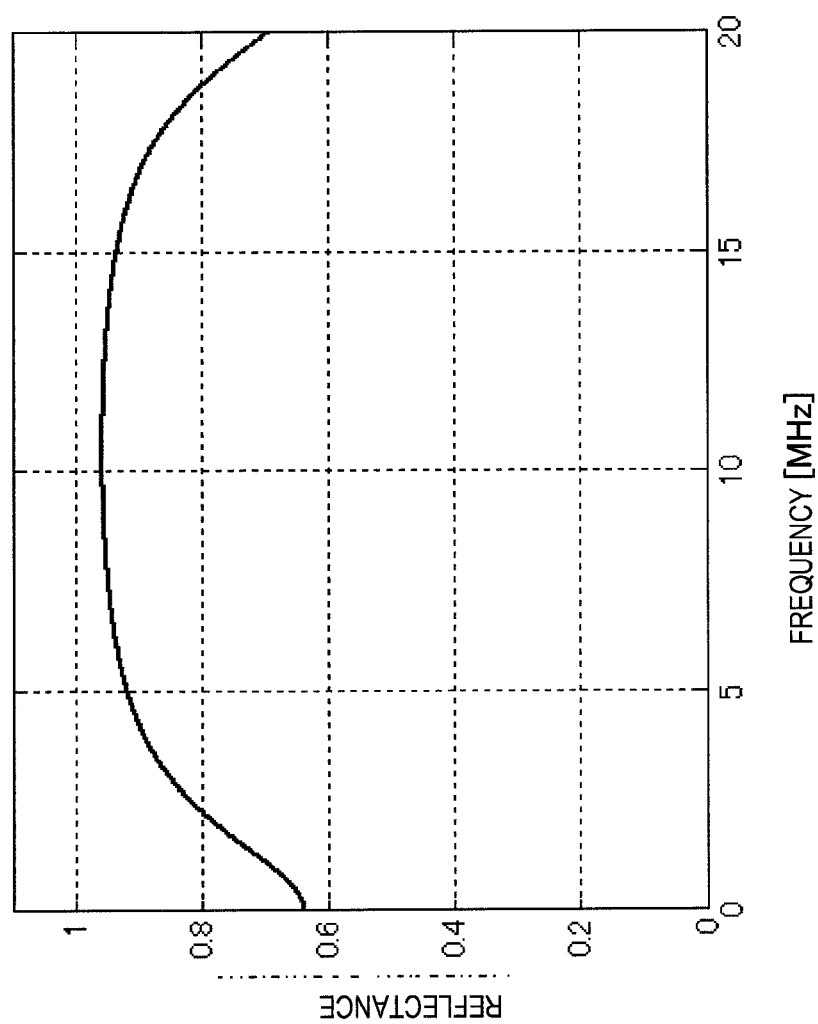
FIG. 7 is a view showing the characteristic curve of frequency and ultrasonic wave reflectance from the boundary between the transducer 11-1 and a backing layer 12.

FIG. 7 is a view showing the characteristic curve of frequency and ultrasonic wave reflectance from the boundary between the transducer 11-1 and the backing layer 12. The characteristic curve of frequency and ultrasonic wave reflectance is calculated under the following conditions.

The transducer 11-1 is formed of silicon including the CMUT chip 18. Representative values of the acoustic impedance and the thickness of the transducer 11-1 are set to 19.7 MRayl and 200 μm, respectively. The reason why the thickness of the transducer 11-1 is set to 200 μm or less is to obtain an ultrasonic image of the body. The center frequency of the ultrasonic wave required to obtain the ultrasonic image of the body is 2 to 14 MHz. In addition, the acoustic lens 14 is formed of silicon rubber. The representative value of the acoustic impedance of the acoustic lens 14 is 1.4 MRayl. In addition, the backing layer 12 is formed of a kneaded mixture of metal and resin. In consideration of matching with the transducer 11-1, the representative value of the acoustic impedance of the backing layer 12 is adjusted to 19.7 MRayl, which is the same value as the acoustic impedance of the transducer 11-1, as described in PTL 2 and PTL 3.

As shown in FIG. 7, the characteristic curve of frequency and ultrasonic wave reflectance reaches 0.90 at the center frequencies of 7.5 MHz and 11 MHz in Table 1 and 0.80 at the center frequency of 2 MHz. That is, this indicates that the influence of multiple reflections is large at all center frequencies since the above values exceed the maximum values Rmax of the reflectance at all center frequencies in Table 1.

Therefore, the subject of the present invention is to make the acoustic impedance of the backing layer 12 and the acoustic impedance of the acoustic lens 14 substantially the same in order to realize the structure capable of suppressing the multiple reflections of reflected waves from the boundary between the transducer 11-1 and the backing layer 12.

In addition, the subject of the present invention can be put in other words in the following respective sections.

(1) An ultrasonic probe having a structure where an acoustic lens, a transducer, and a backing layer are laminated and characterized in that the transducer has a CMUT chip and the backing layer is formed of a material with a value of substantially the same acoustic impedance as the acoustic lens.

(2) The ultrasonic probe described in (1), in which the acoustic impedance of the backing layer is a range for suppressing multiple reflections of an ultrasonic wave.

(3) The ultrasonic probe described in (1) or (2), in which, when the thickness of the transducer in the lamination direction is set to be smaller than 200 μm, the backing layer is formed of a material with a value of acoustic impedance approximating the acoustic impedance of the acoustic lens.

(4) The ultrasonic probe described in any one of (1) to (3), in which the acoustic impedance of the backing layer is acoustic impedance of an object in contact with the acoustic lens.

(5) The ultrasonic probe described in any one of (1) to (3), in which a representative value of the acoustic impedance of the acoustic lens is 1.4 MRayl.

(6) The ultrasonic probe described in any one of (1) to (3), in which the acoustic impedance of the backing layer is 1.1 MRayl to 9.4 MRayl.

(7) The ultrasonic probe described in any one of (1) to (3), in which the thickness of the transducer is equal to or less than 50 μm.

(8) The ultrasonic probe described in (7), in which the acoustic impedance of the backing layer is 3.7 MRayl to 9.4 MRayl.

(9) The ultrasonic probe described in any one of (1) to (3), in which the thickness of the transducer is equal to or less than 25 μm and the acoustic impedance of the backing layer is 3.3 MRayl to 7.9 MRayl.

(10) The ultrasonic probe described in any one of (1) to (3), in which the thickness of the transducer is equal to or less than 10 μm and the acoustic impedance of the backing layer is 1.1 MRayl to 1.8 MRayl.

(11) The ultrasonic probe described in any one of (1) to (3), in which the thickness of the transducer is equal to or less than 5 μm and the acoustic impedance of the backing layer is 2.0 MRayl to 9.4 MRayl.

(12) The ultrasonic probe described in any one of (1) to (3), in which a material of the transducer is silicon, a material of the acoustic lens is silicon rubber, and a material of the backing layer is butyl rubber.

(13) The ultrasonic probe described in any one of (1) to (3), in which the thickness of the transducer is equal to or less than 5 μm and the thickness of an adhesive layer between the transducer and the backing layer is equal to or less than 10 μm.

(14) The ultrasonic probe described in (13), in which the adhesive layer is a die attach film.

(15) An ultrasonic imaging apparatus which includes: an ultrasonic probe that transmits and receives ultrasonic waves to and from an object; an image creation unit that creates an image from signals acquired by the ultrasonic probe; a display unit that displays the image; and a control unit that controls a focal point of the ultrasonic probe according to the depth of a measured portion of the object and which is characterized in that the ultrasonic probe is the ultrasonic probe described in any one of (1) to (14).

Hereinafter, a plurality of embodiments will be described.

First Embodiment

In a first embodiment, cases will be described in which the thickness of the transducer 11-1 is 50 μm, 25 μm, and 10 μm. Since the thickness of the transducer 11-1 became a thickness at which the ultrasonic wave reflectance was less than the theoretical maximum value of the reflectance, 50 μm is set as the reference value of the thickness of the transducer. In addition, 25 μm which is the value of 50% of the reference value is set as the thickness of the transducer, and 10 μm which is the value of 20% of the reference value is similarly set as the thickness of the transducer.

Figure 8:
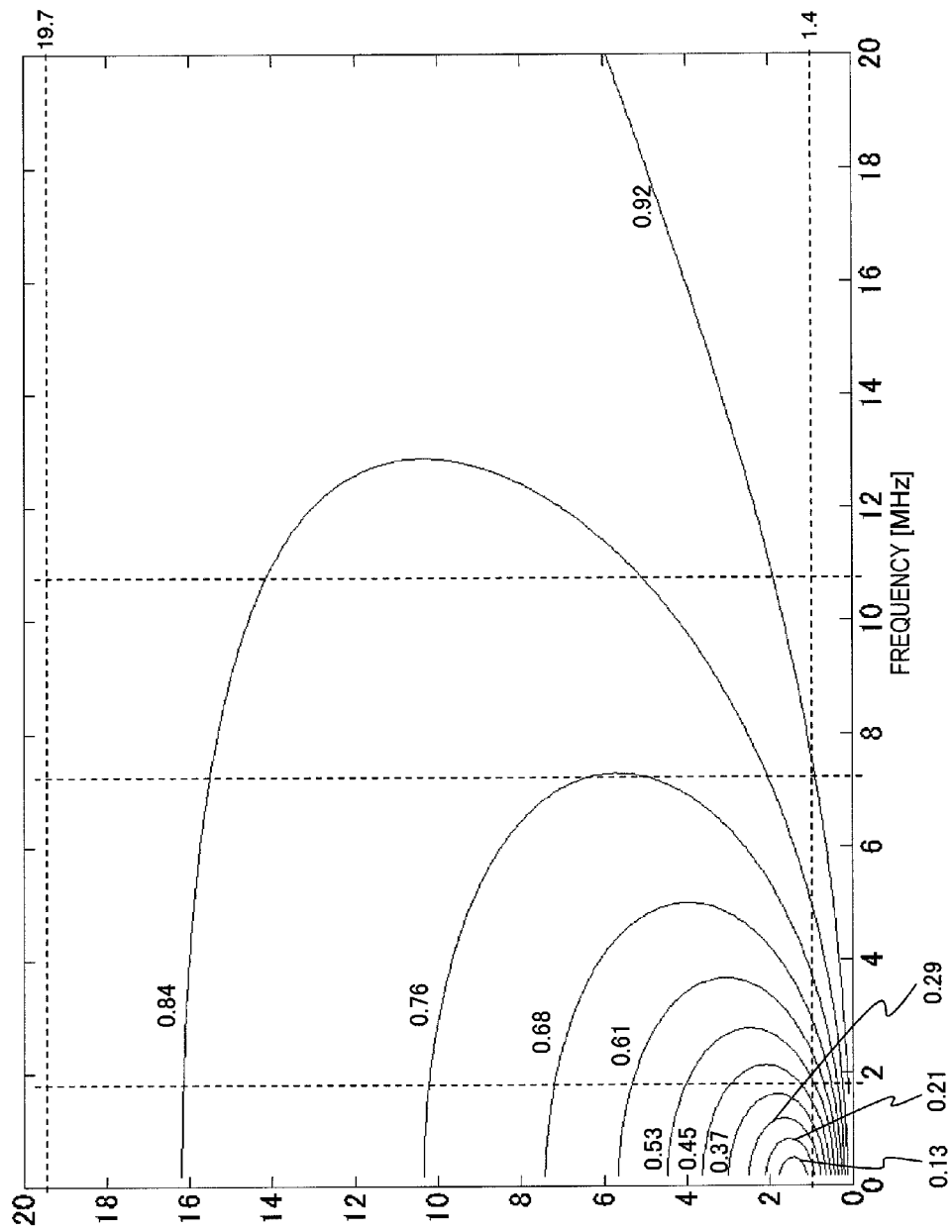
FIG. 8 is a view showing the characteristic curve of frequency and reflectance when the thickness of the transducer 11-1 is set to 50 μm.
Figure 9:
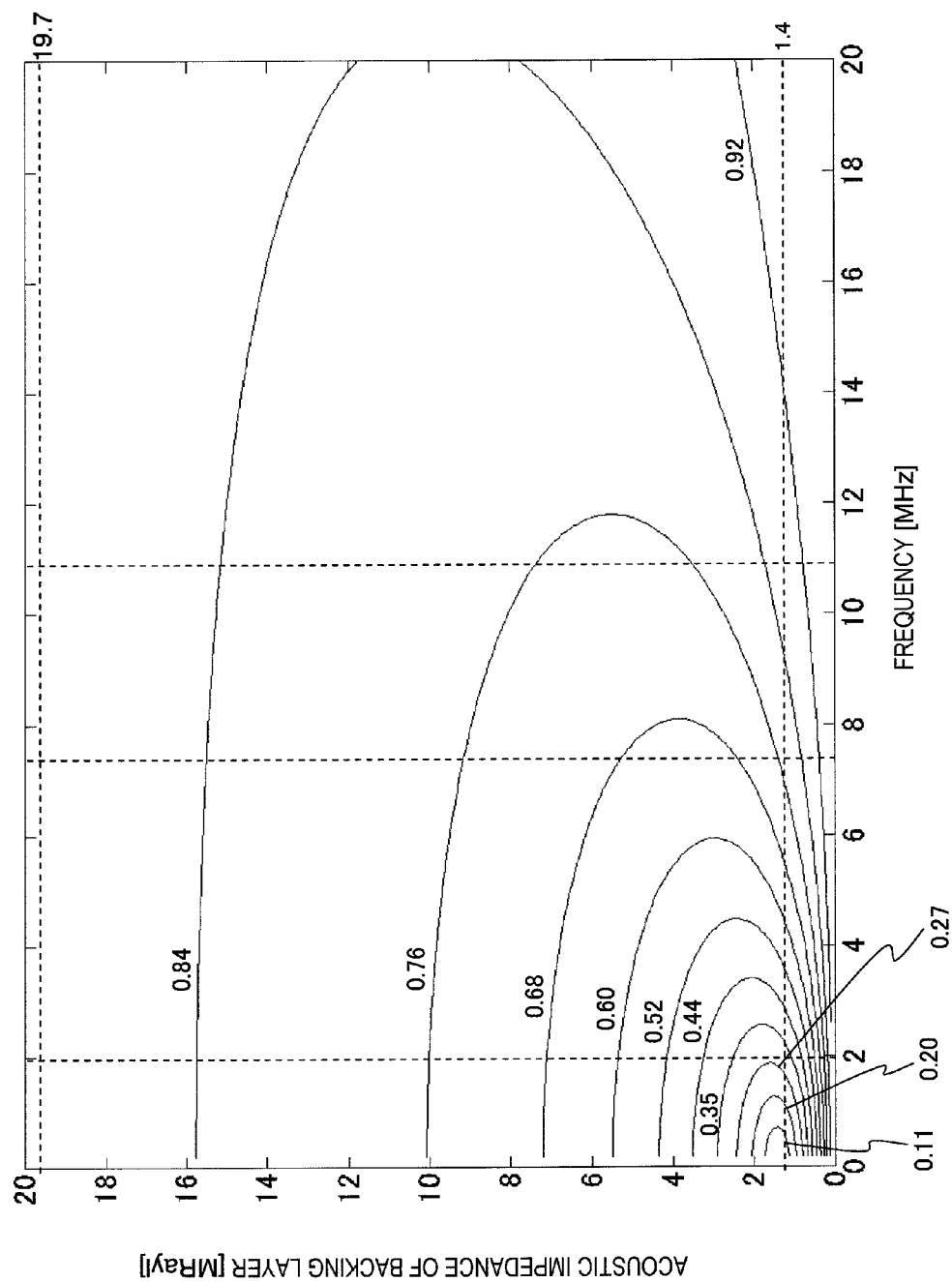
FIG. 9 is a view showing the characteristic curve of frequency and reflectance when the thickness of the transducer 11-1 is set to 25 μm.
Figure 10:
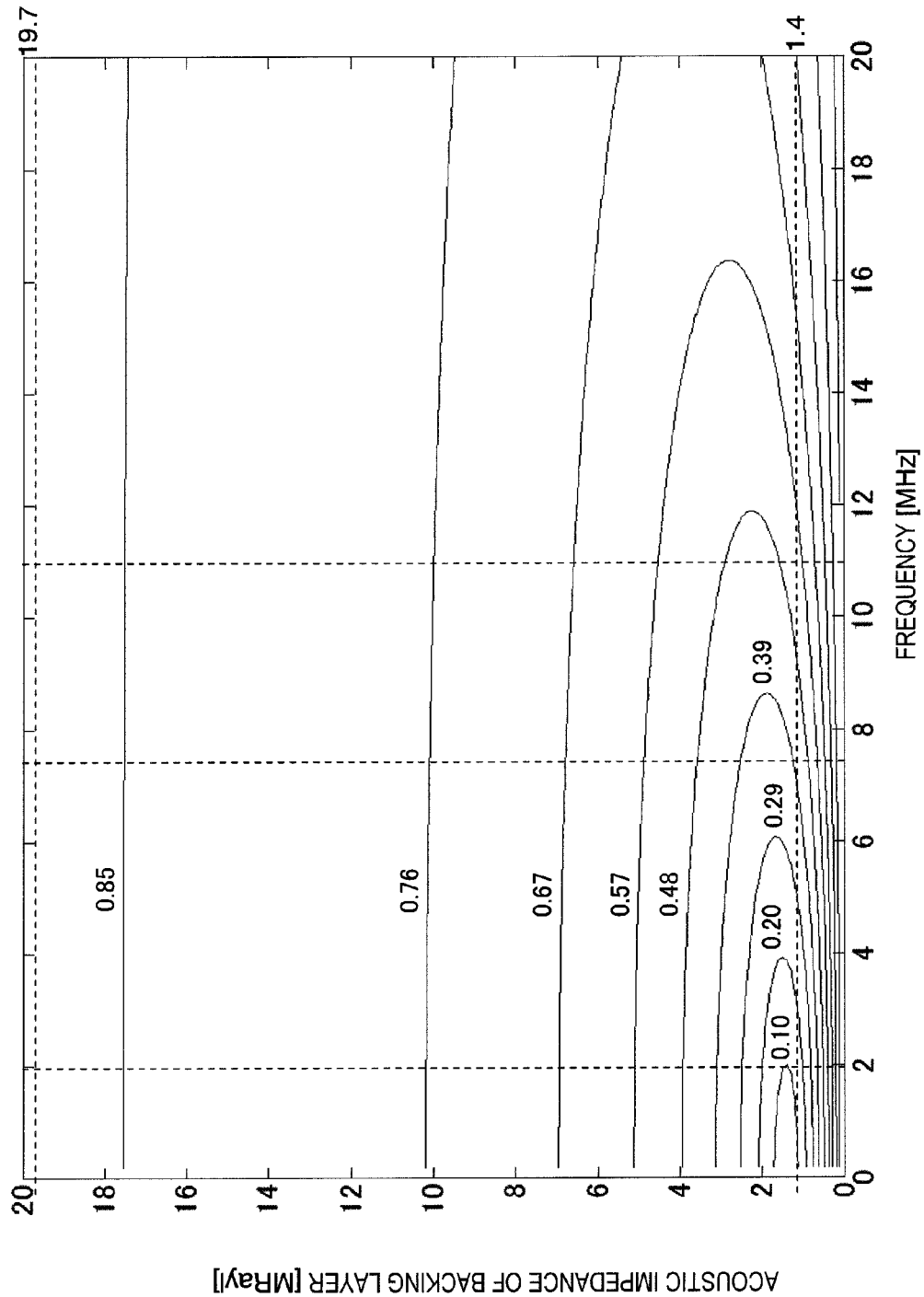
FIG. 10 is a view showing the characteristic curve of frequency and reflectance when the thickness of the transducer 11-1 is set to 10 μm.

FIG. 8 is a graph when the thickness of the transducer 11-1 is set to 50 μm, which shows the calculation result of the ultrasonic wave reflectance when the acoustic impedance value of the backing layer 12 is changed according to the frequency on the horizontal axis. FIG. 9 is a graph when the thickness of the transducer 11-1 in FIG. 8 is set to 25 μm, and FIG. 10 is a graph when the thickness of the transducer 11-1 in FIG. 8 is set to 10 μm.

The material of the transducer 11-1 is silicon with acoustic impedance of 19.7 MRayl, and the material of the acoustic lens 14 is silicon rubber with acoustic impedance of 1.4 MRayl. Since the acoustic lens 14 is a portion in contact with the object, the acoustic impedance of the acoustic lens 14 is set so as to match the acoustic impedance of the object.

First, when the acoustic impedance of the backing layer 12 is set to 19.7 MRayl, it can be seen that the reflectance is much greater than 0.84, that is, the reflectance exceeds the maximum value Rmax of the reflectance, as shown in FIG. 8. In addition, the same tendency is also shown in FIGS. 9 and 10.

Next, when the acoustic impedance of the backing layer 12 is set to 1.4 MRayl which is the same as the acoustic impedance of the acoustic lens 14, it can be seen that the reflectance becomes low as shown in FIG. 8. In addition, the same tendency is also shown in FIGS. 9 and 10.

In addition, as shown in FIGS. 9 and 10, when the thickness of the transducer 11-1 is 25 μm or 10 μm, the conditions of Expression (6) are satisfied. For example, the reflectance is 0.76 or less at the center frequency of 11 MHz. In FIG. 9, the acoustic impedance of the backing layer 12 is in the range of 3.3 MRayl to 7.9 MRayl. In addition, as shown in FIG. 8, when the thickness of the transducer 11-1 is 50 μm, the conditions of Expression (6) are not satisfied.

In addition, when the acoustic impedance of the backing layer 12 is in the range of 3.7 MRayl to 9.4 MRayl in the case where the thickness of the transducer 11-1 is 50 μm, the reflectance is 0.79 or less at the center frequency of 7.5 MHz.

In addition, when the acoustic impedance of the backing layer 12 is in the range of 1.1 MRayl to 1.8 MRayl in the case where the thickness of the transducer 11-1 is 10 μm, the reflectance is 0.17 or less at the center frequency of 2 MHz.

Figure 11:
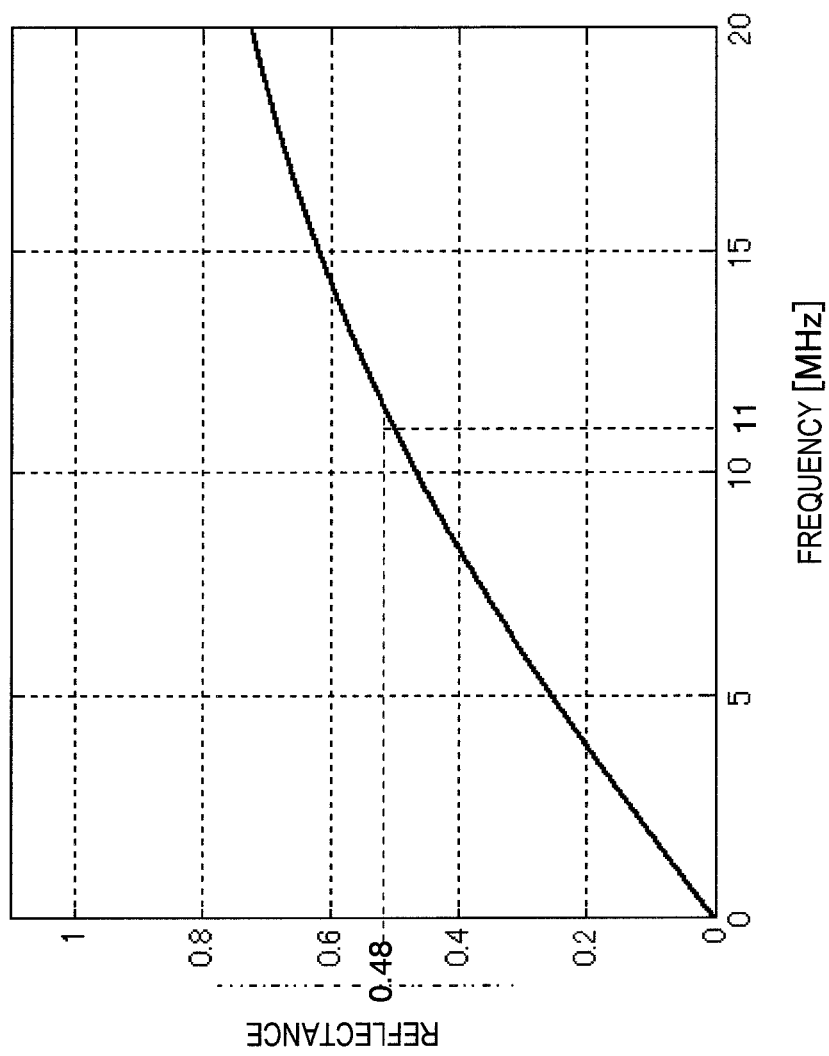
FIG. 11 is a view showing an example of the result obtained by continuously calculating the reflectance with respect to the frequency when the acoustic impedance of the backing layer 12 is set to 1.4 MRayl.

In addition, results obtained by continuously calculating the reflectance with respect to the frequency when the acoustic impedance of the backing layer 12 is set to 1.4 MRayl, which is substantially the same as the acoustic impedance of the acoustic lens 14, will be described. FIG. 11 is a view showing an example of the result obtained by continuously calculating the reflectance with respect to the frequency when the acoustic impedance of the backing layer 12 is set to 1.4 MRayl.

The calculation conditions are as follows. The transducer 11-1 is formed of silicon, the thickness of the transducer 11-1 is set to 10 μm, and the backing layer 12 and the acoustic lens 14 are formed of silicon rubber. In addition, the acoustic impedance of silicon is 19.7 and the acoustic impedance of silicon rubber is 1.4, and the unit is MRayl.

Here, when the thickness of the acoustic lens of the ultrasonic probe is set to 0.7 mm and the center frequency is set to 11 MHz, the maximum value of the reflectance is Rmax=0.50. In the calculation, the maximum value of the reflectance is 0.48 at 11 MHz. Accordingly, it can be seen that Expression (6), which is the conditions to reduce the multiple reflections, is satisfied.

In addition, it can also be defined as Expression (8) that the backing layer 12 and the acoustic lens 14 have substantially the same acoustic impedance.

[Expression 8]

$$\frac{(\text{acoustic impedance of acoustic lens 14}) - (\text{acoustic impedance of backing layer 12})}{\text{acoustic impedance of transducer 11-1}} \ll 1 \quad (8)$$

If Expression (8) is expressed in other words, the value obtained by dividing the absolute value of a difference between the acoustic impedance of the acoustic lens 14 and the acoustic impedance of the backing layer 12 by the acoustic impedance of the transducer 11-1 is much smaller than 1.

As described above, in the first embodiment, in order to suppress multiple reflections of ultrasonic waves, the backing layer is formed of a material with substantially the same acoustic impedance as the acoustic lens. As a result, it is possible to suppress the influence of multiple reflections occurring on the interface of the transducer having a CMUT chip and the backing layer.

In addition, in order to reduce the reflectance in the boundary between the backing layer 12 and the transducer 11-1, it is desirable to set the thickness of the transducer 11-1 as small as possible, for example, to 25 μm and further to 10 μm rather than 50 μm.

Second Embodiment

In a second embodiment, a case will be described in which the thickness of the transducer 11-1 is 5 μm and the backing layer 12 is formed of butyl rubber.

Figure 12:
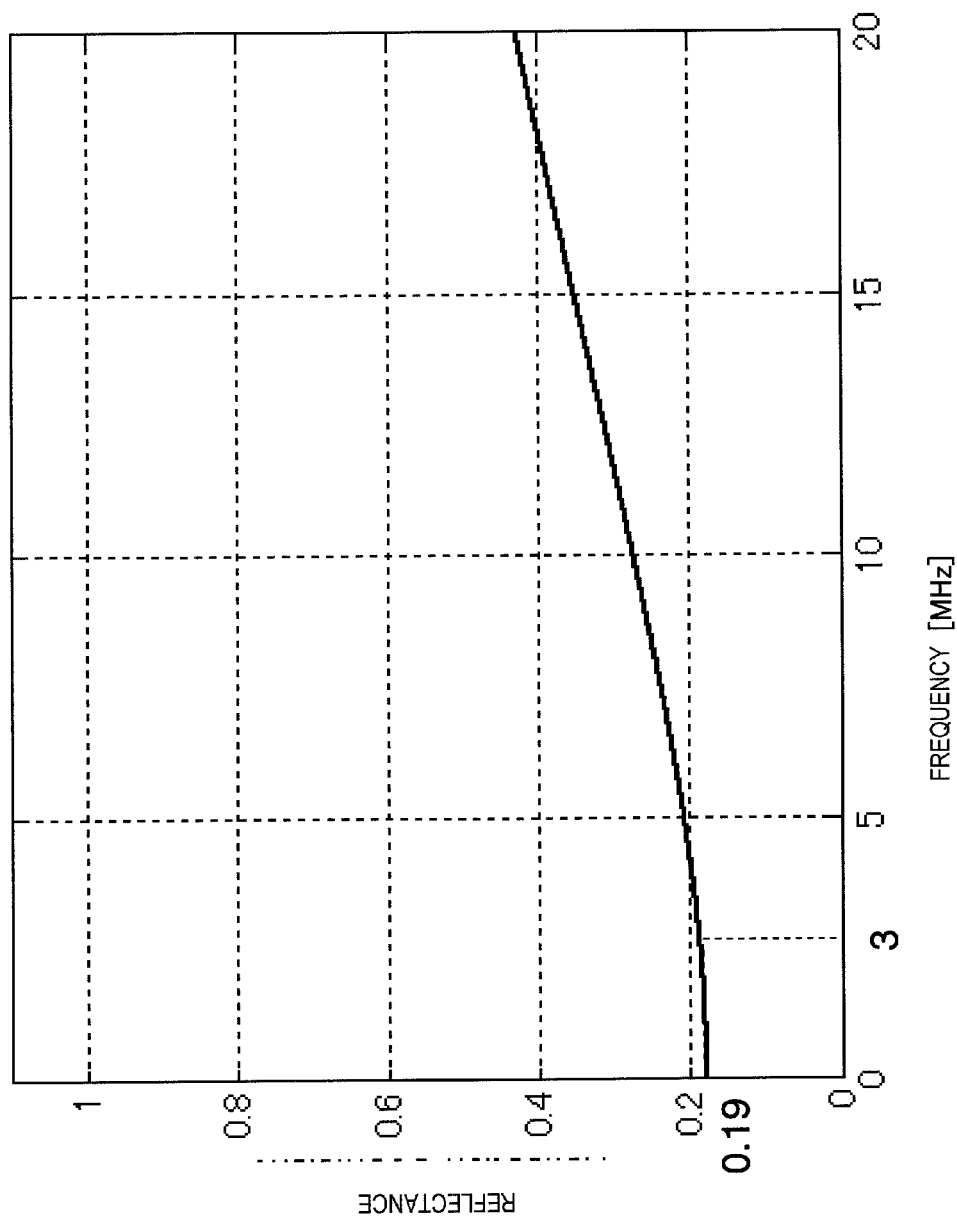
FIG. 12 is a view when the thickness of the transducer 11-1 is set to 5 μm, which shows the calculation result of the ultrasonic wave reflectance when the acoustic impedance value of the backing layer 12 is changed according to the frequency on the horizontal axis.

FIG. 12 is a view when the thickness of the transducer 11-1 is set to 5 μm, which shows the calculation result of the ultrasonic wave reflectance when the acoustic impedance value of the backing layer 12 is changed according to the frequency on the horizontal axis. The material of the transducer 11-1 is silicon, the material of the acoustic lens 14 is silicon rubber, and the material of the backing layer 12 is butyl rubber. In addition, the acoustic impedance of silicon is 19.7, the acoustic impedance of silicon rubber is 1.4, and the acoustic impedance of butyl rubber is 2.0, and the unit is MRayl.

When the thickness of the acoustic lens is set to 1.2 mm and the center frequency of the probe is set to 3 MHz, the maximum value Rmax of the reflectance is 0.23. In the calculation in FIG. 12, the reflectance is 0.19 at 3 MHz. Accordingly, it can be seen that Expression (6), which is the conditions to reduce the multiple reflections, is satisfied.

As described above, in the second embodiment, it is possible to suppress the influence of multiple reflections occurring on the interface of the transducer having a CMUT chip and the backing layer, as in the first embodiment.

In addition, in the second embodiment, the thickness of the transducer 11-1 is set to 5 μm which is smaller than that in the first embodiment. In addition, the acoustic impedance of the backing layer 12 is set to 1.4 times that in the first embodiment. However, by reducing the thickness of the transducer 11-1, it is possible to suppress the influence of multiple reflections occurring on the interface of the transducer having a CMUT chip and the backing layer even if the acoustic impedance of the backing layer 12 is increased.

Accordingly, if the thickness of the transducer 11-1 is reduced, it is possible to select a material with an allowable range of the acoustic impedance of the backing layer 12. In other words, when the thickness of the transducer 11-1 in its lamination direction is set to be smaller, the backing layer 12 can be formed of a material with a value of acoustic impedance that approximates the acoustic impedance of the acoustic lens 14.

Third Embodiment

In a third embodiment, a case will be described in which an adhesive layer 131 is provided between the transducer 11-1 and the backing layer 12.

Figure 13:
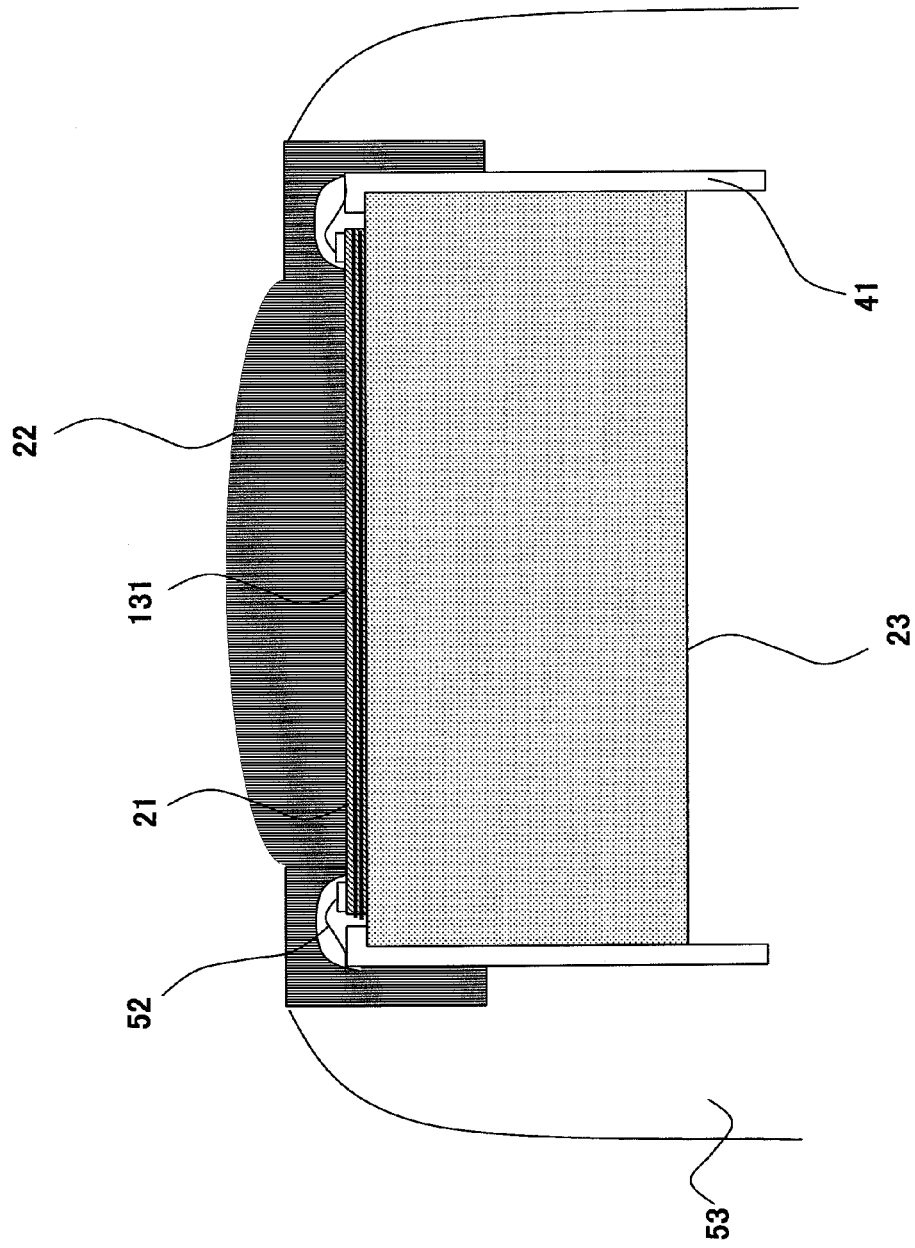
FIG. 13 is a cross-sectional view of an ultrasonic probe of one channel in which an adhesive layer 131 is provided.

FIG. 13 is a cross-sectional view of an ultrasonic probe of one channel in which the adhesive layer 131 is provided.

Materials of the adhesive layer 131 are a die attach film, a silicon adhesive, epoxy resin, and the like, for example.

Assuming that the acoustic impedance of the adhesive layer 131 is $Z_{12}$, the propagation constant of the adhesive layer 131 is $\gamma_{12}$, and the thickness of the adhesive layer 131 is $d_{12}$, the reflectance mr of the ultrasonic wave incident from the acoustic lens 14 side can be expressed by the following Expression (9).

[Expression 9]

$$mr = \frac{\left(1 - \frac{Z_2}{Z_1}\right) + \left(1 + \frac{Z_2}{Z_1}\right)\left(\frac{Xa - Ya}{Xb + Yb}\right)}{\left(1 + \frac{Z_2}{Z_1}\right) + \left(1 - \frac{Z_2}{Z_1}\right)\left(\frac{Xa - Ya}{Xb + Yb}\right)} \quad (9)$$

$$\begin{cases} X = \frac{Z_{12}}{Z_1}(c + d) \\ Y = c - d \\ a = c^{-r_1 d_1} \\ b = e^{+r_1 d_1} \\ c = e^{-r_{12} d_1} \\ d = \frac{Z_3 - Z_{12}}{Z_3 + Z_{12}} e^{-r_{12}(d_1 + 2d_{12})} \end{cases}$$

Figure 14:
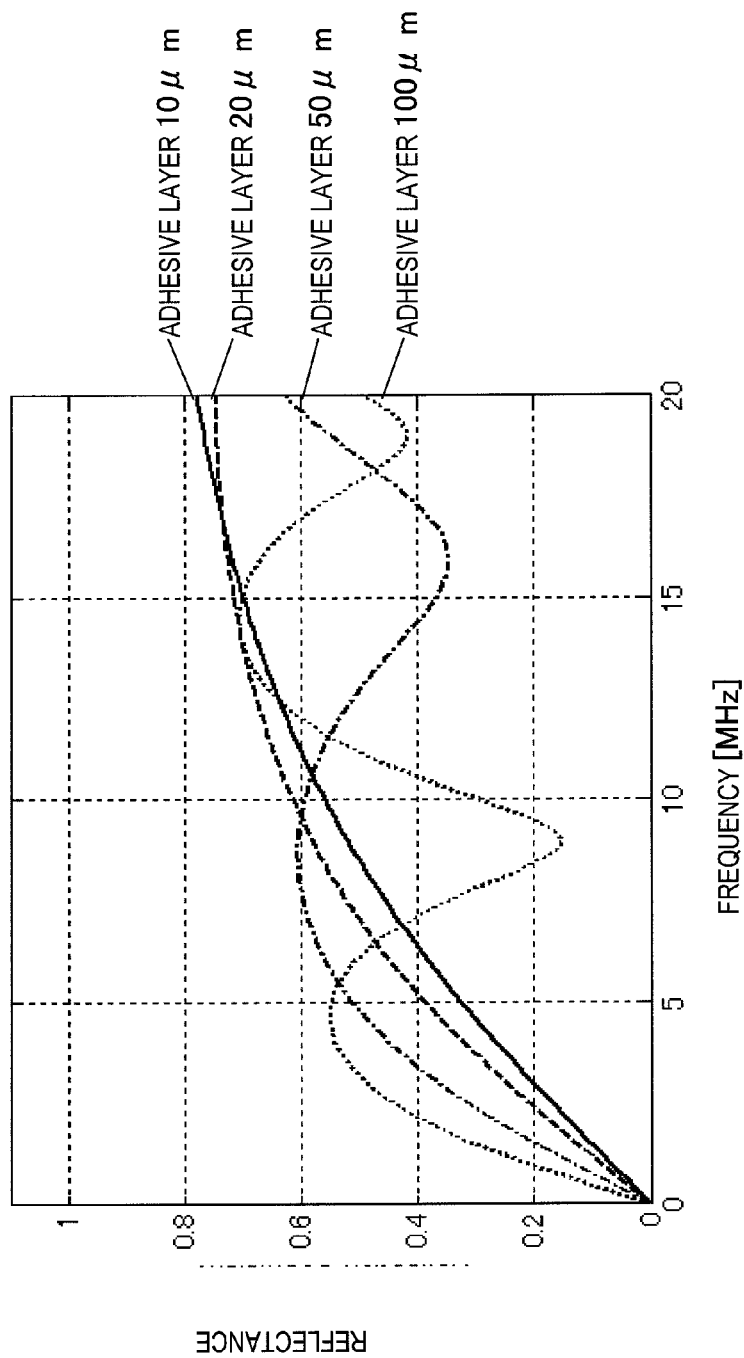
FIG. 14 is a view showing the ultrasonic wave reflectance mr in the transducer 11-1 when the thickness of the adhesive layer 131 between the transducer 11-1 and the backing layer 12, and the center frequency of the ultrasonic wave from the transducer 11-1 are changed.

FIG. 14 is a view showing the ultrasonic wave reflectance mr in the transducer 11-1 when the thickness of the adhesive layer 131 between the transducer 11-1 and the backing layer 12 and the center frequency of the ultrasonic wave from the transducer 11-1 are changed. In the example shown in FIG. 14, the thickness of the adhesive layer 131 is changed to 10 μm, 20 μm, 50 μm, and 100 μm. In addition, the material of the transducer 11-1 is silicon, the thickness of the transducer 11-1 is 10 μm, the material of the acoustic lens 14 and the backing layer 12 is silicon rubber, and the material of the adhesive layer 131 between the transducer 11-1 and the backing layer 12 is a die attach film. In addition, the acoustic impedance of silicon is 19.7, the acoustic impedance of silicon rubber is 1.4, and the acoustic impedance of the die attach film is 2.5, and the unit is Mrayl. As the thickness of the adhesive layer 131 increases, the reflectance is locally reduced at a specific frequency. In the example shown in FIG. 14, the reflectance is locally reduced near 16 MHz when the thickness of the adhesive layer 131 is 50 μm and near 9 MHz and 18 MHz when the thickness of the adhesive layer 131 is 100 μm.

In addition, local reductions in the reflectance cannot be seen when the thickness of the adhesive layer 131 is 10 μm and 20 μm. The cause of the local reduction in the reflectance has been found to be the resonance on the upper and lower interfaces of the die attach film. Since the resonance causes ringing noise at the time of transmission and reception of ultrasonic waves, the resonance affects the pulse characteristics. Therefore, in order to reduce noise, it is desirable to set the thickness of the adhesive layer 131 small, for example, to 50 μm and 20 μm and further to 10 μm rather than 100 μm.

Figure 15:
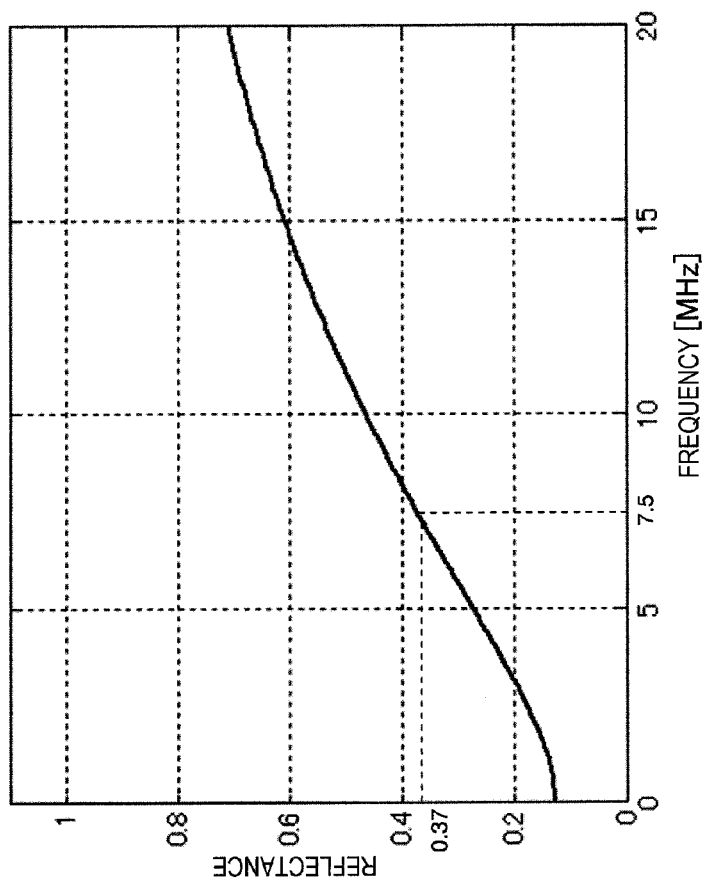
FIG. 15 is a view showing an example of continuous calculation of the reflectance with respect to the frequency when the thickness of the adhesive layer 131 is set to 5 μm.

In addition, results obtained by continuously calculating the reflectance with respect to the frequency when the thickness of the adhesive layer 131 is set to 5 μm will be described. FIG. 15 is a view showing an example of continuous calculation of the reflectance with respect to the frequency when the thickness of the adhesive layer 131 is set to 5 μm.

The calculation conditions are as follows.

The material of the transducer 11-1 is silicon, the thickness of the transducer 11-1 is 10 μm, the material of the acoustic lens 14 is silicon rubber, the material of the backing layer 12 is polyethylene, and the material of the adhesive layer 131 between the transducer 11-1 and the backing layer 12 is a die attach film. In addition, the acoustic impedance of silicon is 19.7, the acoustic impedance of silicon rubber is 1.4, and the acoustic impedance of polyethylene is 1.8, and the unit is Mrayl.

When the thickness of the acoustic lens is set to 1.0 mm and the center frequency of the probe is set to 7.5 MHz, the maximum value Rmax of the reflectance is 0.56. In the calculation shown in FIG. 15, the reflectance is 0.37 at 7.5 MHz. Accordingly, it can be seen that Expression (6), which is the conditions to reduce the multiple reflections, is satisfied.

As described above, in the third embodiment, it is possible to suppress the influence of multiple reflections occurring on the interface of the transducer having a CMUT chip and the backing layer, as in the first embodiment.

In addition, in the third embodiment, the influence of the acoustic characteristics at the time of transmission and reception of ultrasonic waves can be suppressed by reducing the thickness of the adhesive layer 131 between the CMUT chip 18 and the backing layer 12. Accordingly, it is possible to reduce the reflectance while improving the pulse characteristics.

REFERENCE SIGNS LIST 11-1 to 11-*m*: transducer
12: backing layer
14: acoustic lens
18: CMUT chip

The invention claimed is:

1. An ultrasonic probe comprising:
a structure including an acoustic lens, a transducer, and a backing layer that are laminated,
wherein the transducer has a CMUT chip, a thickness of the transducer in a lamination direction is set to be smaller than 200 µm,
wherein the backing layer is formed of a material with a substantially same value of acoustic impedance as the acoustic lens, and
wherein the acoustic impedance of the backing layer is a range for suppressing multiple reflections of an ultrasonic wave, so as to suppress the multiple reflections of a boundary between the transducer and the backing layer.

2. The ultrasonic probe according to claim 1, wherein the acoustic impedance of the backing layer is acoustic impedance of an object in contact with the acoustic lens.

3. The ultrasonic probe according to claim 1, wherein a representative value of the acoustic impedance of the acoustic lens is 1.4 MRayl.

4. The ultrasonic probe according to claim 1, wherein the acoustic impedance of the backing layer is 1.1 MRayl to 9.4 MRayl.

5. The ultrasonic probe according to claim 1, wherein a thickness of the transducer is equal to or less than 50 µm.

6. The ultrasonic probe according to claim 5, wherein the acoustic impedance of the backing layer is 3.7 MRayl to 9.4 MRayl.

7. The ultrasonic probe according to claim 1, wherein a thickness of the transducer is equal to or less than 25 µm, and the acoustic impedance of the backing layer is 3.3 MRayl to 7.9 MRayl.

8. The ultrasonic probe according to claim 1, wherein a thickness of the transducer is equal to or less than 10 µm, and the acoustic impedance of the backing layer is 1.1 MRayl to 1.8 MRayl.

9. The ultrasonic probe according to claim 1, wherein a thickness of the transducer is equal to or less than 5 µm, and the acoustic impedance of the backing layer is 2.0 MRayl to 9.4 MRayl.

10. The ultrasonic probe according to claim 1, wherein a material of the transducer is silicon, a material of the acoustic lens is silicon rubber, and a material of the backing layer is butyl rubber.

11. The ultrasonic probe according to claim 1, wherein a thickness of the transducer is equal to or less than 5 µm, and a thickness of an adhesive layer between the transducer and the backing layer is equal to or less than 10 µm.

12. The ultrasonic probe according to claim 11, wherein the adhesive layer is a die attach film.

13. An ultrasonic imaging apparatus comprising:
an ultrasonic probe that transmits and receives ultrasonic waves to and from an object;
an image creation unit that creates an image from signals acquired by the ultrasonic probe;
a display unit that displays the image; and
a control unit that controls a focal point of the ultrasonic probe according to a depth of a measured portion of the object,
wherein the ultrasonic probe is the ultrasonic probe according to claim 1.

14. The ultrasonic probe according to claim 1, wherein the transducer is disposed adjacent to the backing layer.

* * * * *